United States Patent
Chen et al.

(10) Patent No.: US 11,540,724 B2
(45) Date of Patent: Jan. 3, 2023

(54) REAL-TIME 3D MICROWAVE MONITORING OF THERMAL THERAPY

(71) Applicant: UNIVERSITY OF SOUTHERN CALIFORNIA, Los Angeles, CA (US)

(72) Inventors: Guanbo Chen, Los Angeles, CA (US); Mahta Moghaddam, Los Angeles, CA (US); John Stang, Los Angeles, CA (US); Mark Haynes, Los Angeles, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 828 days.

(21) Appl. No.: 16/469,047

(22) PCT Filed: Jan. 4, 2018

(86) PCT No.: PCT/US2018/012410
§ 371 (c)(1),
(2) Date: Jun. 12, 2019

(87) PCT Pub. No.: WO2018/129204
PCT Pub. Date: Jul. 12, 2018

(65) Prior Publication Data
US 2020/0093374 A1    Mar. 26, 2020

Related U.S. Application Data

(60) Provisional application No. 62/442,340, filed on Jan. 4, 2017.

(51) Int. Cl.
*A61B 5/01* (2006.01)
*A61B 5/0507* (2021.01)
(Continued)

(52) U.S. Cl.
CPC ............ *A61B 5/015* (2013.01); *A61B 5/0507* (2013.01); *A61B 18/04* (2013.01);
(Continued)

(58) Field of Classification Search
CPC .......... A61B 18/1815; A61B 2018/183; A61B 2018/1838; A61B 2018/1846;
(Continued)

(56) References Cited

U.S. PATENT DOCUMENTS 6,275,738 B1 *   8/2001   Kasevich ........... A61B 18/1815
                                                                607/101
2004/0240512 A1 *  12/2004  Pesach ................. G01K 13/20
                                                                374/161
(Continued)

OTHER PUBLICATIONS

Gao et al. "Sensitivity of the Distorted Born Iterative Method to the Initial Guess in Microwave Breast Imaging", Aug. 2015, IEEE transactions on antennas and propagation, vol. 63, pp. 3540-3547 (Year: 2015).*

(Continued)

*Primary Examiner* — Linda C Dvorak
*Assistant Examiner* — Nicholas S Borsch
(74) *Attorney, Agent, or Firm* — Snell & Wilmer LLP

(57) ABSTRACT

A method for determining a change of temperature of an object. The method may include heating an object and measuring scattering parameters (S-parameters) of scattered microwave electric fields from the object. A distorted Born iterative method may be used to determine a change of a dielectric property of the object based on the measured S-parameters. A change of temperature of the object may be determined based on the change of the dielectric property of the object.

26 Claims, 10 Drawing Sheets

(51) Int. Cl.
*A61B 18/04* (2006.01)
*A61B 18/18* (2006.01)
*A61B 18/20* (2006.01)
*A61B 18/00* (2006.01)
*A61B 18/22* (2006.01)

(52) U.S. Cl.
CPC ............... *A61B 18/1815* (2013.01); *A61B 2018/00803* (2013.01); *A61B 2018/183* (2013.01); *A61B 2018/20353* (2017.05); *A61B 2018/2261* (2013.01)

(58) Field of Classification Search
CPC .... A61B 2018/1853; A61B 2018/1823; A61B 2018/1861; A61B 2018/1869; A61B 2018/1876; A61B 2018/1884; A61B 2018/1892; A61B 5/0507
See application file for complete search history.

(56) References Cited

U.S. PATENT DOCUMENTS

2011/0152853 A1* 6/2011 Manley ............. A61B 18/1815
606/41
2013/0135136 A1 5/2013 Haynes et al.

OTHER PUBLICATIONS

International Search Report and Written Opinion of the International Searching Authority (dated Apr. 27, 2018) for Corresponding International PCT Patent Application No. PCT/US18/012410, filed Jan. 4, 2018.

Haynes, Mark et al., "Real-time microwave imaging of differential temperature for thermal therapy monitoring", IEEE Transactions on Biomedical Engineering, Jun. 2014, vol. 61, No. 6, pp. 1787-1797 See abstract; and pp. 1787-1788, 1790-1791, 1795.

Rossman, Christian et al. "Review of temperature dependence of thermal properties, dielectric properties, and perfusion of biological tissues at hyperthermic and ablation", Critical Reviews in Biomedical Engineering, 2014, vol. 42, Issue 6, pp. 467-492 (internal pp. 1-31) See the whole document.

Gao, Fuqiang et al. "Sensitivity of the distorted born iterative method to the initial guess in microwave beast imaging", IEEE Transactions on Antennas and Propagation, 2015, vol. 63, Issue 8, pp. 3540-3547 (internal pp. 1-8) See the whole document.

Meaney, Paul M. et al., "Microwave thermal imaging of scanned focused ultrasound heating: phantom results", International Journal of Hyperthermia. See the whole document.

Chen, Guanbo et al., "Real-time 3D microwave monitoring of interstitial thermal therapy", IEEE Transactions on Biomedical Engineering, Mar. 2018 (online published: May 8, 2017), vol. 65, Issue 3, See the whole document.

* cited by examiner

REAL-TIME 3D MICROWAVE MONITORING OF THERMAL THERAPY

CROSS-REFERENCE TO RELATED APPLICATIONS

This application claims the benefit of U.S. Provisional Application No. 62/442,340, filed Jan. 4, 2017, the entire contents of which are hereby incorporated by reference.

BACKGROUND

In recent years, thermal therapies have seen increased use in the treatment of a variety of diseases, particularly in cases of soft tissue cancers. Thermal therapies can be classified into two types: hyperthermia and thermal ablation. The first type, hyperthermia, commonly defined as heating tissues from 40° C. to 47° C. for tens of minutes, causes irreversible damage to cancer cells by altering the permeability of plasma membranes and denaturing proteins. Hyperthermia has shown therapeutic benefit as an adjuvant to radiotherapy and chemotherapy, as well as inducing both apoptotic and necrotic cell death given a sufficient thermal dose. The latter type, thermal ablation, employs more extreme temperatures over a shorter period to induce rapid and localized tissue destruction. Ablative methods, which include cryoablation, high intensity focused ultrasound (HIFU), radio frequency ablation (RFA), microwave ablation, and laser ablation, offer the potential to treat lesions that are not surgically accessible via traditional means due to the morbidity or mortality associated with surgical excision.

In both hyperthermia and ablation, thermal monitoring is necessary to ensure the accuracy of both treatment location and thermal dose, and a number of different methods of varying complexity have been reported. In the simplest application of RFA, ultrasound is used to guide the placement of an invasive probe, but no monitoring of thermal dose is employed. Similarly, laboratory and clinical studies of a system using an invasive electric-field probe to focus within a compressed breast were reported. Fiber optic sensors have been used in several systems to monitor thermal dose, but coverage is limited to the sensor tip and inherently invasive. For full coverage of the treatment region, Proton Resonance Frequency Shift (PRFS) Magnetic Resonance Thermal Imaging (MRTI) has been used, as in MR-guided phased arrays, but the expense, complexity and compatibility of using MRI has limited its use.

SUMMARY

Improvements in the field of thermal monitoring are desired. In embodiments disclosed herein, apparatuses, systems and methods for real-time 3D microwave thermal imaging are disclosed. An "Exemplary Result" utilizing processes according to this application is also disclosed herein. The Exemplary Result tests the methods disclosed herein with simulated monitoring of thermal therapy.

Apparatuses, systems and methods disclosed herein may utilize a distorted Born iterative method (DBIM). Compared with methods using a Born approximation (BA), the DBIM based method solves the forward problem for a nonlinear inversion and may provide a better total field approximation inside a monitored region. Further, DBIM may utilize evanescent waves and multiple scattering effects to provide improved resolution. Further, a developed conformal finite-difference time-domain (FDTD) solver is disclosed herein, which provides capability and flexibility to dynamically import the dielectric material and update the forward model in each iteration.

In embodiments disclosed herein, graphic processing unit (GPU) parallel computing may be utilized to accelerate the computation of both the forward and inverse problem to achieve realtime imaging.

In the "Exemplary Result" section, methods disclosed herein are validated with simulation of monitoring thermal therapy. Comparison of the reconstructed temperature map using BA and DBIM are provided and discussed. With DBIM, the average estimation error of the mean temperature within the region of interest (ROI) may be reduced from 2.5 to 1.0 degrees for the noise-free case, and from 2.9 to 1.7 degrees for the 2% background noise case. The maximum relative pixel error within the entire monitored region from 2.7% with BA to 1.8% may be improved with DBIM for the noise-free case, and from 4.4% to 3.4% for the 2% background noise case.

Embodiments disclosed herein include a method for determining a change of temperature of an object. The method may comprise heating an object in a monitored region. Scattering parameters (S-parameters) of scattered microwave electric fields from the object may be measured. A dielectric background and electric field of the monitored region may be iteratively updated based on the measured S-parameters. A change of a dielectric property of the object may be determined based on the updated dielectric background and the updated electric field. A change of temperature of the object may be determined based on the change of the dielectric property of the object.

Embodiments disclosed herein include a method for determining a change of temperature of an object. The method may comprise heating an object. S-parameters of scattered microwave electric fields from the object may be measured. A distorted Born iterative method (DBIM) may be utilized to determine a change of a dielectric property of the object based on the measured S-parameters. A change of temperature of the object may be determined based on the change of the dielectric property of the object.

Embodiments disclosed herein include a system comprising one or more antennas configured to receive scattered microwave electric fields from an object in a monitored region, and a controller. The controller may be configured to measure S-parameters of the scattered microwave electric fields; iteratively update a dielectric background and electric field of the monitored region based on the measured S-parameters; determine a change of a dielectric property of the object based on the updated dielectric background and the updated electric field; and determine a change of temperature of the object based on the change of the dielectric property of the object.

BRIEF DESCRIPTION OF THE DRAWINGS

Features and advantages of the systems, apparatuses, and methods as disclosed herein will become appreciated as the same become better understood with reference to the specification, claims, and appended drawings wherein:

DETAILED DESCRIPTION

The present disclosure is directed to apparatuses, systems, and methods of thermal monitoring. The thermal monitoring may be utilized in treatment of patients, such as cancer patients or other forms of patient, or may be used in other non-medical applications.

The apparatuses, systems, and methods disclosed herein may be utilized in thermal therapy. In one embodiment the thermal therapy may comprise interstitial thermal therapy. In other embodiments other forms of thermal therapies may be applied. The thermal therapies may be applied for medical treatment, or other forms of therapeutic uses. In other embodiments, other forms of heating (non-thermal therapy) may be applied and monitored according to apparatuses, systems and methods herein.

In one embodiment, the thermal therapy may be used to treat cancer patients and particularly cancer tissues. Unlike more common cancers with widely available screening tools (e.g. breast and prostate cancer), soft tissue, bone, and brain cancers are often difficult or impossible to remove with traditional surgical resection. In the case of brain lesions, stereotactic radiotherapy (e.g. Gamma Knife or proton beam) is sometimes used when surgical resection is not possible; however, these therapies are limited to small tumors, can require surgical attachment of a guidance frame, and use highly specialized equipment only available in a limited number of hospitals due to cost and space requirements. Additionally, certain tumor types such as high grade glial neoplasms that account for as much as fifty percent of primary central nervous system tumors are not responsive to stereotactic radiation. In other embodiments, other forms of cancer tissues (non-brain) may be treated.

Figure 1:
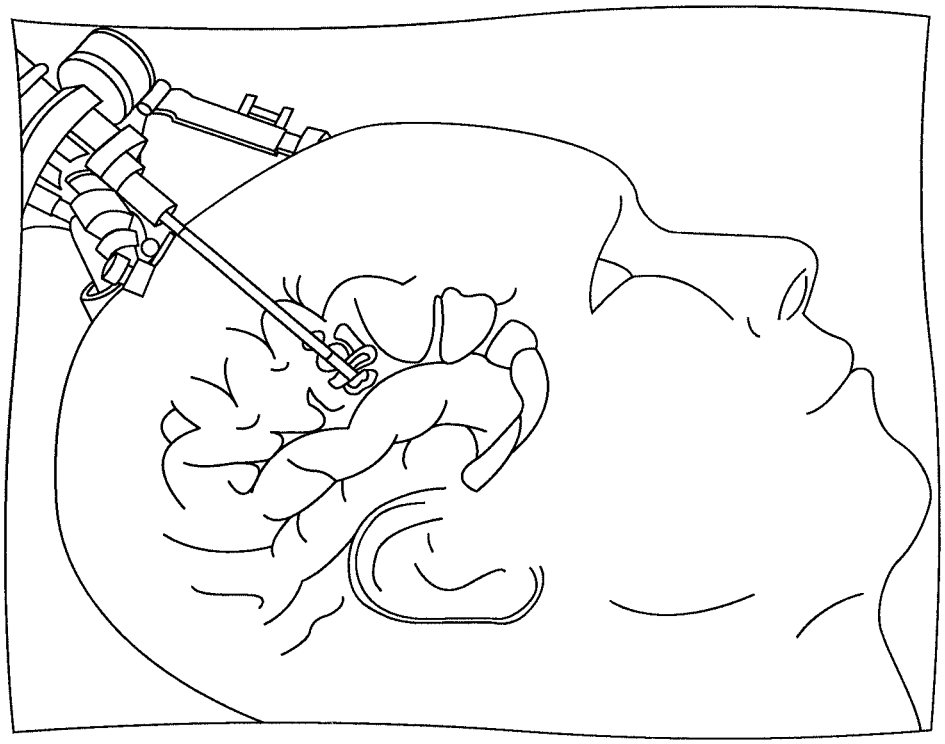
FIG. 1 illustrates a representation of a probe delivering heat.
Figure 2:
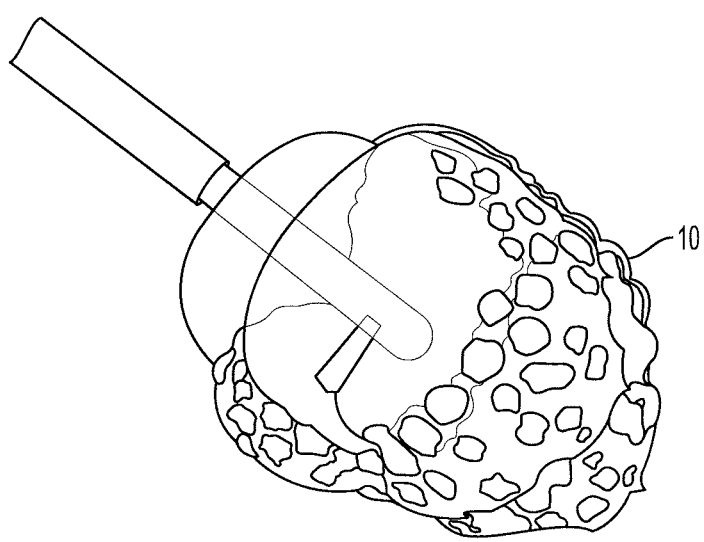
FIG. 2 illustrates a representation of a probe delivering heat.

The thermal therapy may take any form, including but not limited to the hyperthermia and thermal ablation methods disclosed herein. The thermal therapies may include ablative methods such as cryoablation, high intensity focused ultrasound (HIFU), radio frequency ablation (RFA), microwave ablation, and laser ablation, among others. The heating methods may be performed by respective heating elements (e.g., radio transmitters, antennas, lasers, probes, heating coils). In one embodiment, laser-induced interstitial thermal therapy (LITT) may be utilized (as represented in FIGS. 1 and 2). This method has seen increased use in the treatment of surgically inaccessible lesions 10. Such a procedure currently relies on MRI for planning, targeting, monitoring, and verification, which, while highly precise, limits its use to locations and times where access to MRI machines is affordable and available. The thermal monitoring disclosed herein may be utilized with this form of interstitial thermal therapy treatment, among others.

The apparatuses, systems, and methods disclosed herein may be utilized in microwave thermal imaging. Such microwave thermal imaging may be in real-time and may be in 3D. Microwave thermal imaging may be utilized for non-invasive temperature monitoring. This thermal monitoring method may be predicated on using microwaves to image small changes in the dielectric properties of tissue with temperature. When tissue is heated during thermal therapy, the change of tissue dielectric property produces a change in the scattered microwave electric fields that can be measured in the form of S-parameters. These S-parameters are linked back to the dielectric property of the tissue with an electric field volume integral equation (VIE). In methods utilizing a Born approximation (BA), a FEM solver of Ansys HFSS may be used to compute the incident electric field inside the monitored region, and the BA may be adopted to construct a pre-computed linear inversion matrix, which solves the VIE in real-time.

However, while this method using the BA is an effective approach for validating the concept of real time microwave thermal monitoring, the linear Born approximation in the inversion may restrict the usage of this method to the cases when the change of temperature is small. When change of temperature is large, using the incident field to approximate the total field in the VIE may no longer be valid and may lead to inaccurate reconstruction. In addition, utilizing Ansys HFSS as the forward problem solver may pose difficulties in constructing and dynamically updating the forward model during the monitoring process, which may make it impractical for clinical use.

The apparatuses, systems, and methods herein may utilize a microwave thermal monitoring algorithm using the nonlinear Distorted Born Iterative Method (DBIM). Compared with the BA method described above, DBIM may provide a better approximation of the total electric field within the VIE, may account for the multiple scattering effects and may utilize the evanescent wave information, which in turn may produce a more accurate nonlinear inversion result, especially when the temperature change is large. A conformal finite difference time domain (CFDTD) method may be used as an efficient and accurate forward problem solver, which addresses the modeling issue of HFSS and provides the capability to dynamically update the forward model required by DBIM during the monitoring process. Furthermore, this method may reduce the systematic measurement drift error in calculating the differential S-parameter, as the time lapse between the total and incident S-parameter measurements is reduced. Finally, Graphic Processing Unit (GPU) parallel computing may be used to accelerate the computation of both forward and inverse problems. Given sufficient computational power, the forward scattering model can be updated in real-time throughout a thermal therapy procedure.

Microwave thermal imaging is based on the principle of using microwaves to measure relatively small changes that occur in the dielectric properties of materials, especially those with water content, as a result of changes in temperature. In an embodiment in which the heated object is tissue, the dielectric properties of the tissue, especially tissue with significant water content, may be measured. Multiple studies have been performed to characterize the change in the dielectric properties of water at microwave frequencies as a function of temperature. In particular, within the range of thermal therapy temperatures, the dielectric change of animal liver tissue has been reported to be approximately 1% per C.° at 915 MHz. When the dielectric property is changed with temperature, it produces a change in the scattered electric fields that can then be measured in the form of S-parameters between a series of transmit and receive antenna pairs arranged around the treatment region to be monitored.

Figure 3:
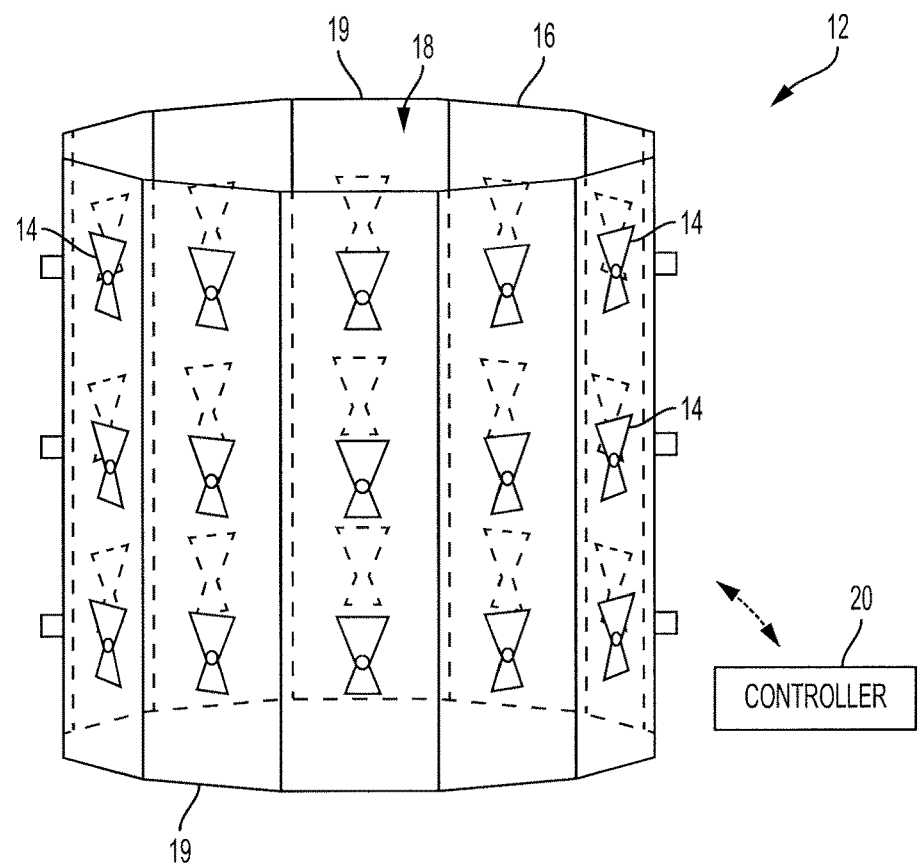
FIG. 3 illustrates a perspective view of a system, according to an embodiment of the present disclosure.

FIG. 3, for example, illustrates a perspective view of a system 12 that may be utilized to perform methods disclosed herein. The system 12 may include a plurality of antennas 14 configured to transmit and receive scattered microwave electric fields from an object in a monitored region. The antennas 14 may be positioned on a support structure 16 that forms a cavity 18 for receiving the object to be monitored. The object is not shown in FIG. 3. The support structure 16 may include a plurality of panels 19 (twelve panels 19 are shown in FIG. 3) positioned around the cavity 18. The antennas 14 may be positioned in a spaced relationship on the support structure 16 around the cavity 18. In FIG. 3, thirty-six antennas 14 are shown. In other embodiments, a different number of antennas 14 or different configuration of support structure 16, cavity 18, or antenna 14 may be utilized as desired.

The antennas 14 may each be configured to transmit or receive scattered microwave electric fields, or may be configured to perform both operations. In one embodiment, one or more antennas 14 may be utilized. In an embodiment in which one antenna is utilized, the antenna may be configured to both transmit and receive scattered microwave electric fields.

A controller 20 may be configured to perform the processes disclosed in this application. The controller 20 may be configured to communicate with the one or more antennas 14 and may be configured to measure S-parameters of the scattered microwave electric fields. The controller 20 may be configured to include a processor configured to perform the processes disclosed in this application, which may include a graphic processing unit (GPU). The controller 20 may include a memory to store data for use by the processor. The systems disclosed herein may additionally include one or more heating elements (e.g., radio transmitters, antennas, lasers, probes, heating coils) for heating the object.

Figure 4:
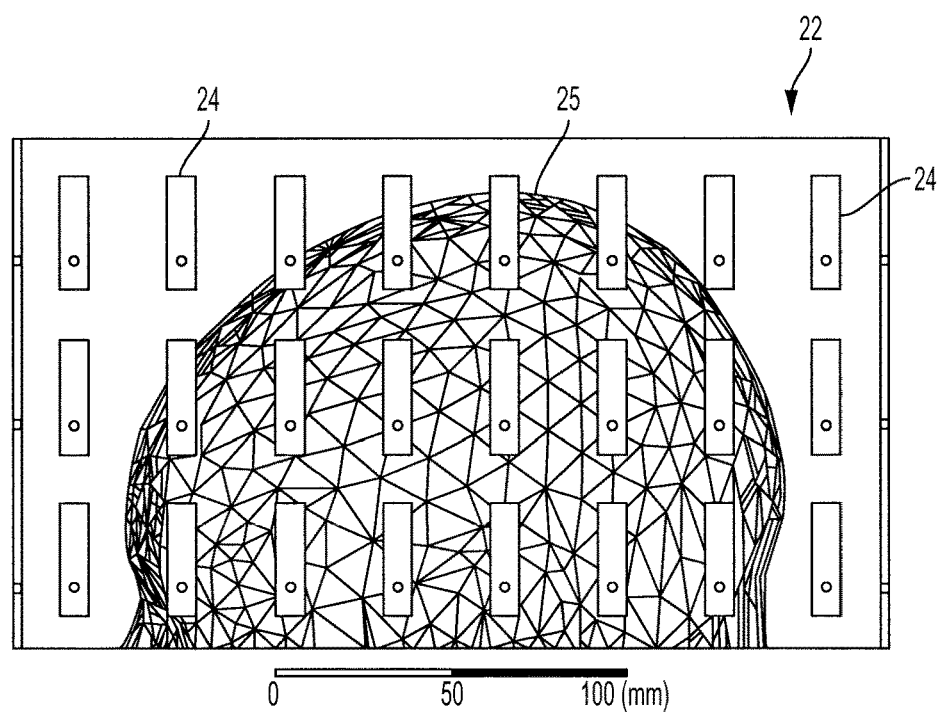
FIG. 4 illustrates a perspective view of a system, according to an embodiment of the present disclosure.

FIG. 4 illustrates a perspective view of a system 22 that may be utilized to perform the methods disclosed herein. The system 22 may include a plurality of antennas 24 configured to transmit and receive scattered microwave electric fields from an object in a monitored region. Here, the object comprises a brain lesion. A representation of a head 25 is shown relative to the antennas 24 and in the cavity of the system, and the head contains the brain lesion. Thermal therapy of the brain lesion may be provided and monitoring of the thermal therapy of the brain lesion may be provided by the system. In other embodiments, other configurations of systems and objects to be monitored may be provided.

In microwave imaging, S-parameters are linked back to the dielectric property of the object to be monitored (e.g., the tissue) with an electric field volume integral equation (VIE). In certain methods, the Born approximation (BA) is adopted in solving this VIE, which approximates the total field in the VIE with the incident field. However, this approach may only be valid when the change of temperature is small. The methods disclosed herein utilize methods in which the DBIM is used, which refreshes the background dielectric property and the electric field in the monitored region in each iteration. Thus, the DBIM may provide a better approximation of the total field within the VIE than BA and yields a more accurate reconstruction result, especially when the temperature change is large.

A challenge in using the more accurate DBIM method is twofold: first, in the added complexity of passing the updated object properties from the inversion step back to the forward problem solver and dynamically updating the forward model in the monitoring process; second, in the computational power necessary to solve the forward and inverse problem while still achieving real-time imaging. According to methods herein, these issues may be addressed respectively by: (1) the use and integration of a developed conformal FDTD forward solver into the real-time imaging algorithm, which may add capability of solving the forward problem during the monitoring process (indicated by solid vs. dotted line path in FIG. 5) and may provide a better approximation of the total field in the VIE; (2) the use of GPU parallel computing to accelerate solving both the forward and inverse problems, which may enable real-time imaging with the state-of-the-art GPU computation power.

Figure 5:
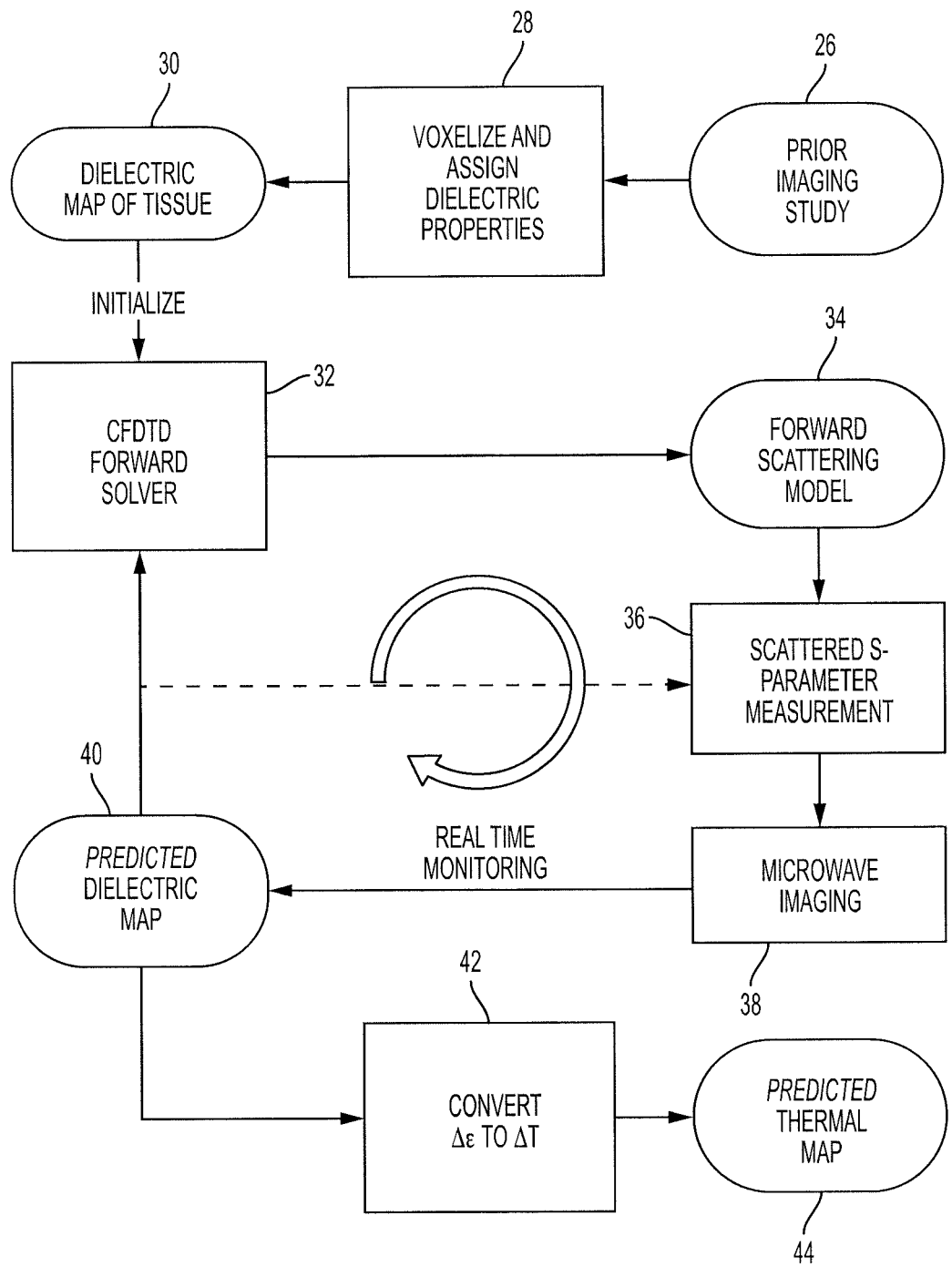
FIG. 5 illustrates a flow-chart of a method according to an embodiment of the present disclosure.

The steps in implementing this DBIM-based microwave thermal monitoring method may be as follows. With reference to FIG. 5, first, the dielectric properties of the object to be heated (e.g., tissue) before heating are determined. This is represented by step 26 in FIG. 5. The dielectric properties of the object (e.g., tissue) before heating may be derived from prior imaging studies. For example, the properties may be derived from the relative brightness of voxels in a CT/MR image and/or from the fat-to-water ratio computed from methods such as MRI IDEAL. In other embodiments, other methods of determining the dielectric properties of the tissue may be provided. A dielectric map may be produced, as is represented in steps 28 and 30 of FIG. 5. In one embodiment, the dielectric map may be a voxelized dielectric map. This dielectric map may be used as the initial background in the inversion, sub-sampled on the grid of the CFDTD forward solver, and then used to construct the initial waveport numerical vector Green's function for inversion. In one embodiment, a nearest point interpolation may be used to map the initial background dielectric information from prior imaging studies to an optimal forward solver mesh. The CFDTD forward solver may be provided in step 32 of FIG. 5, and the forward scattering model may be updated in step 34 of FIG. 5.

The object (e.g., tissue) is heated in a monitored region. During the heating, the monitored heated object produces scattered microwave electric fields. In an embodiment utilizing thermal therapy, during the thermal therapy the heated object (e.g., tissue) that is illuminated by the incident waves (produced by one or more antennas or other component of the monitoring apparatus) produces scattered microwave electric fields. The scattered microwave electric fields may be measured in the form of S-parameters. A Vector Network Analyzer (VNA) may measure the S-parameters. The VNA may be part of a controller such as a controller 20 shown in FIG. 3. The measurement of the S-parameters are represented in step 36 of FIG. 5.

DBIM is used to solve the nonlinear inverse scattering problem with the S-parameters and to reconstruct the differential change of the dielectric of the object (e.g., tissue). Both the dielectric background and the total electric fields within the VIE are refreshed when the forward problem is solved in the DBIM. The microwave imaging is represented in step 38 of FIG. 5, the predicted dielectric map is represented in step 40 of FIG. 5, and the solution of the forward problem and the update of the forward scattering model are represented in steps 32 and 34 of FIG. 5 respectively. It is noted that this process may occur iteratively as represented by the curved arrow shown in FIG. 5.

The dielectric background and electric field of the monitored region may be iteratively updated based on the measured S-parameters. Then, the differential change of the dielectric property of the object may be determined. The change of the dielectric property may be determined based upon the updated dielectric background and the updated electric field. This may be in accordance with the DBIM process and may utilize the electric field volume integral equation. The differential change of the dielectric constant may then be mapped to the change of temperature to produce the image of heat change. This is represented as step 42 in FIG. 5 to produce the predicted thermal map 44. The change of the temperature of the object may be determined based on the determined change of the dielectric property of the object. The output of the change of temperature may be provided in any desired format, such as a 3D map, or other form of output (e.g., chart, graph) as desired. The steps of FIG. 5 may be performed in real-time during heating of the object. The output may be provided on a display screen or the like. The output may be provided in real-time during the heating. In other embodiments, the steps of FIG. 5 may be varied as desired.

The forward scattering model uses the reciprocity principle to link the measured S-parameters to the dielectric properties of the monitored region. This may be done by using a numerical vector Green's function kernel with waveport excitation in the volume integral equation. This waveport vector Green's function may contain all scattering interactions between the background object, imaging cavity, and source excitation, effectively providing the system with an absolute characterization. In addition, this waveport vector Green's function may be fully integrated into the conformal FDTD forward solver and accounts for S-parameters between transmitters and receivers with different modes, geometries and impedances. The VIE with the numerical vector Green's function is given by, $$S_{m,n}^{scat}(\omega) = k_b^2 \int O(r') G_{m,n}(r',\omega) \cdot E_n(r',\omega) dV' \quad (1)$$

where r' is the imaging region position vector. The vector $E_n$ is the total field in the imaging region due to the transmitter n. The quantity $k_b$ is the lossless background wavenumber with $k_b^2 = \omega^2 \mu_0 \in_b$, and $\in_b$ is the background permittivity with $\in_b = \in_0 \in_{rb}$, where $\in_{rb}$ is the background relative permittivity. The dielectric constant function O is defined as $$O(r') = \Delta \epsilon(r') + \frac{\Delta \sigma(r')}{j\omega \epsilon_b}, \quad (2a)$$

-continued $$\Delta \epsilon(r) = \frac{\epsilon(r) - \epsilon_b}{\epsilon_b} \quad (2b)$$

$$\Delta \sigma(r) = \sigma(r) - \sigma_b \quad (2c)$$

where $\Delta\in(r')$ and $\Delta\sigma(r')$ are the change of permittivity and conductivity in the heating region relative to the background. The numerical vector Green's kernel is defined as, $$G_{m,n}(r',\omega) = \frac{jE_m^b(r',\omega)\sqrt{Z_n(\omega)}}{\omega\mu_0 \int_{A_n} e_n^t(r) \times \bar{h}_n^t(r) f(\omega) \cdot dA \sqrt{Z_m(\omega)}} \quad (3)$$

where the integration in the denominator is over the surface area $A_n$ of the transmitting waveport n, $f(\omega)$ is the frequency domain response of the source signal waveform, $e_n^t$ and $h_n^{-t}$ are the electric and magnetic field mode template used to excite transmitting port n in the CFDTD solver, which produces a uni-directional propagating wave into the waveport. The vector $E_m^b$ is the total field in the heat monitoring region when exciting receiver m with the desired magnetic field mode template $h_m^{-t}$. By choosing the electric and magnetic field mode template to excite the transmitting and receiving waveport respectively, the scattered S-parameter between two ports with the desired modes may be acquired. In the case of coaxial feeds that may be used in the heat monitoring system, the TEM field mode template is used for both the transmitting and receiving ports. In addition, $Z_m(\omega)$ and $Z_n(\omega)$ are used to characterize the transmitting and receiving ports with different impedances.

During the imaging of temperature change in the monitored region, $E_m^b$ and $E_n$ are updated in each iteration. Substituting (3) into (1) and reorganizing the equation, the VIE becomes $$S_{m,n}^{scat}(\omega) = C(\omega) k_b^2 \int O(r') E_m^b(r',\omega) \cdot E_n(r',\omega) dV' \quad (4)$$

where $$C(\omega) = \frac{j\sqrt{Z_n(\omega)}}{\omega\mu_0 \int_{A_n} e_n^t(r) \times \bar{h}_n^t(r) f(\omega) \cdot dA \sqrt{Z_m(\omega)}} \quad (5)$$

The newly derived VIE (5) provides an absolute source characterization of the thermal monitoring system, and provides the ability to directly use the measured S-parameters to solve inverse scattering problem and perform microwave imaging of the monitored region.

In certain embodiments, it may be advantageous to solve the forward problem at a lower rate than the image refresh rate. This may depend on the computational power available and the microwave measurement speed. An asynchronous processing method may be utilized. Therefore, to distinguish between these two refresh rates in the case of asynchronous imaging, i frames may be defined as those in which the thermal image is refreshed and j frames as those in which the forward scattering model is refreshed. Each i frame and each j frame may occur asynchronously. The forward solver and the inversion may be run in parallel and re-synchronized in every j frame. This may improve the frame-rate in microwave imaging and may assist to achieve real-time monitoring while solving the forward problem during inversion.

Therefore, from equation (4), the VIE to be solved when refreshing each imaging frame during thermal monitoring may be represented as $$\Delta S_{m,n}^{ij} = Ck_b^2 \int \Delta O^i(r') E_m^{bj}(r') \cdot E_n^j(r') dV' \qquad (6)$$

where i stands for the $i^{th}$ frame that the S-parameters are measured, the change of the tissue dielectric property is solved in the inverse problem, and the temperature change in the monitored region is refreshed. The index j stands for the $j^{th}$ frame that the forward problem is solved with the most recent estimated object dielectric property, $O^i$. From this solution, the $E_n^j$, $E_m^{bj}$ in the monitored region and the incident field S-parameters $S_{,nm}^j$, are updated. Meanwhile, by solving the inverse problem at the $j^{th}$ frame, the new reconstruction background $O^j$ of the monitored region may be acquired. Thus, in every $j^{th}$ step, both the electric fields within the VIE and the reconstruction background, $O^j$, are refreshed. The forward model is updated every j frame. These forward model parameters may then be used in all subsequent i frames until the next j frame.

The differential scattered S-parameter used in solving for the temperature change in each image frame is given by $$\Delta S_{m,n}^{ij} = S_{m,n}^i - S_{m,n}^j \qquad (7)$$

where $\Delta S_{m,n}^{ij}$, stands for the differential scattered S-parameter which is the difference between the S-parameter measured in the current monitoring frame i and the S-parameter measured in the $j^{th}$ frame when the forward problem was most recently solved. With $\Delta S_{m,n}^{ij}$, equation (6) may be used to solve the object material contrast $\Delta O^{ij}$ between the $j^{th}$ frame and the current frame i. The process of solving (6) is described further below regarding the cost function (equation (10)). From $\Delta O^{ij}$, the current tissue material property is $$O^i = O^j + \Delta O^{ij} \qquad (8)$$

Then, object material contrast $\Delta O^{ij}$ may be mapped to get the temperature change $\Delta T^{ij}$ between the $i^{th}$ frame and $j^{th}$ frame, and find the current temperature:

$$T^i = T^j + \Delta T^{ij} \qquad (9)$$

Throughout the imaging process, both the total electric field within the VIE and the differential imaging background are updated in every j frame, which is essentially the distorted Born iterative method. The iterative update of the dielectric background and the electric field may occur asynchronously with the determination of the change of the dielectric property of the object.

To estimate the dielectric map using equation (6), the cost function may be formulated that measures the difference between the forward modeling and the measurement data, $$F(m) = \|Gm - d\|_D^2 + \|m\|_M^2 \qquad (10)$$

where $\|Gm - d\|_D^2$ is the weighted $L_2$ norm of the difference between the right-hand-side and left-hand-side of equation (6). Vector d represents the measured differential scattered S-parameter. The complex vector in contains the differential dielectric property of the monitored region. The matrix G is a linear operator which links the object dielectric properties to the S-parameters. The term $\|m\|_M^2$ is used to smooth the imaged differential object and serves as a regularization term. The weighted vector norms $\|\cdot\|_D$ and $\|\cdot\|_M$ are defined by the inverse data and model covariance matrix $C_D^{-1}$ and $C_M^{-1}$, where $C_D^{-1}$ can be interpreted as the measurement noise and $C_M^{-1}$ can be interpreted as the uncertainty in the forward model. To solve equation (10), the conjugate gradient (CG) method may be utilized. Model parameters and search direction updates are given by $$m_{i+1} = m_i - \alpha_i v_i \qquad (11)$$

$$v_i = \gamma_i + \beta_i v_{i-1} \qquad (12)$$

where i is the CG iteration, v is the search direction, and $\alpha$ is the step length. The quantity $\gamma$ is the steepest decent vector and is related to the gradient g of the cost function by $\gamma = C_M g$. The coefficient $\beta$ is chosen so that the current gradient of the cost function is linearly independent from all previous gradients. Here the Polak and Ribiere expressions for $\beta$ may be utilized:

$$\beta^i = \frac{\gamma^{*i} C_M^{-1} (\gamma^i - \gamma^{i-1})}{\gamma^{*i-1} C_M^{-1} \gamma^{i-1}} \qquad (13)$$

The value of the step length $\alpha$ may be obtained through a linear search that minimizes the cost function along the search direction given by $$\alpha^i = \frac{\gamma^{*i-1} C_M^{-1} v^i}{(Gv^i) * C_D^{-1} (Gv^i)} \qquad (14)$$

If every measurement datum and image pixel are independent; and the measurement noise and pixel uncertainties are constant, then the covariance matrix $C_D^{-1}$ and $C_m^{-1}$ are equal to scalars $1/\sigma_d^2$ and $1/\sigma_m^2$, respectively. If $\lambda = \sigma_d/\sigma_m$, then the cost function can be simplified to, $$F(m) = \|Gm - d\|^2 + \lambda^2 \|m\|^2 \qquad (15)$$

where the term $\lambda^2 \|m\|^2$ serves as the common Tikhonov regularization. This may also be solved with the conjugate gradient method described above, while each iteration requires less computation. In the "Exemplary Results" section of application, equation (15) is used as the cost function in the inversion.

A DBIM-based asynchronous differential scattering algorithm for thermal monitoring that may be used in embodiments of the disclosure is listed below. This algorithm includes two parts: part 1 (i frames) solves the linear inverse problem, updates the change of dielectric material and refreshes the thermal monitoring frame in real time; part 2 (j frames) runs the forward solver with the most recent material estimate, refreshes the differential imaging background and updates the electric field in the monitored region, which provides a better linear approximation for the non-linear inverse problem. Part 1 and Part 2 of the algorithm may run in parallel, and they communicate through the variable Flag. When Flag=1, the forward solver in Part 2 is finished. Part 2 then waits until the current inversion in Part 1 has finished. With Parts 1 and 2 mutually paused, object and field updates are swapped: the forward solver receives the latest object estimate from Part 1, and the inversion receives the latest electric fields and background material from Part 2. After the swap is complete, Flag=0 is set and the two parts run independently again.

---

Algorithm 1 DBIM thermal monitoring algorithm:
Solving inverse problem

1: Initialize j = 0, $T^j$ = body temperature, $O^j$ = unheated background material, Flag = 0
2: Run FDTD in unheated background, store $E_m^{bj}$, $E_n^j$, $S_{m,n}^j$
3: for i = 1 to N do
4:     Measure $S_{m,n}^i$, $\Delta S_{m,n}^{ij} = S_{m,n}^i - S_{m,n}^j$ -continued Algorithm 1 DBIM thermal monitoring algorithm:
Solving inverse problem 5:   Solve Eq. (6) for $\Delta O^{ij}$ with CG, $O^i = \Delta O^{ij} + O^j$
6:   Map $\Delta \epsilon$ to $\Delta T$, $T^i = T^j + \Delta T$
7:   if Flag == 1 then
8:      j = j'
9:      $O^j = O^{j'}$, $S^j = S^{j'}$, $E_m^{bj} = E_m^{bj'}$, $E_n^{bj} = E_n^{bj'}$, update VIE
10:     j' = i
11:     $O^{j'} = O^i$
12:     Flag = 0
13:  end if
14: end for Algorithm 2 DBIM thermal monitoring algorithm:
Running forward solver 1: if i < start frame then
2:   wait ( )
3: end if
4: j' = i
5: $O^{j'} = O^i$
6: while i < N do
7:   if Flag == 0 then
8:      Run FDTD with new $O^{j'}$ containing new background
        material $\epsilon_b^{j'}$ and $\sigma_b^{j'}$, Store $E_m^{bj'}$, $E_n^{bj'}$, $S^{j'}$
9:      Flag = 1
10:  else
11:     wait ( )
12:     goto Step 6
13:  end if
14: end while Achieving real-time imaging for thermal monitoring is predicated on how fast the forward and inverse problems are solved. In certain embodiments, the cost-effective parallel computing capability of GPUs may be utilized to accelerate the computation of both forward and inverse problems. A GPU may perform iterative update of the dielectric background and the electric field in parallel with the determination of the change of the dielectric property of the object being measured.

Compared with CPU, GPU has many more cores, while each core has a simpler architecture and less cache. Essentially, GPUs devote many more transistors to data processing rather than data caching and flow control, which may make them suitable for single program multiple data (SPMD) type parallelism. When solving the forward problem disclosed herein, the conformal FDTD method may be used, which is suitable for this type of parallel computing because it has a relatively simple calculation in each Yee cell and a large number of cells need to be solved. A limitation with GPU computing may be the limited cache memory within each core and the high cost to fetch data from global memory to the cores and even higher cost to fetch data from CPU RAM. As FDTD is a stencil-like problem, the parallel computing of the algorithm may be optimized by storing the data that can be reused in the next time step in the shared memory to reduce the high latency from accessing global memory. In addition, when the updated total electric field in the imaging domain is too large to be stored in the GPU global memory, it may be transferred from GPU memory to CPU RAM asynchronously during FDTD computation, which hides the high latency of transferring data from GPU to the CPU RAM. For the inverse problem, most of the computation lies in matrix-vector and vector-vector multiplication for constructing the VIE and running the conjugate gradient solver, which are also highly suitable for parallel computation using GPU.

In one embodiment of a parallel computing implementation, an Nvidia Tesla C2075 GPU may be utilized with 448 cores and a peak 1 Teraflop computation speed using single precision. In a FDTD simulation, for a region with 85×54× 85 Yee cells and 10 thousand time steps, the GPU accelerated code may finish one transmitter calculation in 12 seconds, which is equivalent to a FDTD computation speed of 325 million cells per second. In solving the inverse problem, the GPU accelerated VIE construction and conjugate gradient algorithm requires less than 0.5 seconds to solve 2000 unknowns in 30 iterations. With a Pascal GPU with 10 Tera-flops single precision computation speed and a newly developed NVlink to boost the communication between GPU and CPU memory by a factor of 5 to 12, the FDTD solver can solve for one transmitter within 1 second. As each transmitter excitation is independent of each other, with enough GPUs one may solve the whole forward problem in approximately 1 second, thus allowing for improved ability to image in real-time.

In one embodiment, two buffer regions may be provided in GPU RAM. The two buffer regions may address a problem of limited size of GPU memory and may reduce the latency of transferring data from GPU RAM to CPU RAM. The two buffer regions may be referred to as "Buffer 1" and "Buffer 2." Buffer 1 at first may be used to store the total field calculated by the FDTD. Meanwhile, the total fields stored in Buffer 2 may be transferred from GPU RAM to CPU RAM. After Buffer 1 is filled up, then the total fields stored in the Buffer 1 may be transferred to the CPU RAM, while the Buffer 2 may be used to store the incoming newly calculated total fields from the FDTD solver.

Although the use of GPUs is disclosed herein, in other embodiments other forms of processors may be utilized to perform the methods disclosed herein. Such GPUs (or other forms of processors) may be included in a controller, such as the controller 20 shown in FIG. 3.

The methods disclosed herein may be embodied in software, firmware, hardware, and/or may be embodied in a controller such as the controller 20 shown in FIG. 3. The methods may be incorporated on a non-transitory computer readable medium. The methods may be stored in a memory such as RAM, ROM, a hard disk, flash memory, or other forms of memory. In certain embodiments, the methods may be performed remotely from other portions of the system (e.g., separate from the one or more antennas). In certain embodiments, the methods may be performed in a mobile device, such as a remote scanner device or a mobile medical device for use to measure temperature. A stationary device is also contemplated. Other physical implementations of the methods disclosed herein may be utilized.

The apparatuses, systems, and methods disclosed herein may be used in a medical application (as disclosed herein regarding treatment of tissue or cancer cells), or may be used in non-medical applications. The apparatuses, systems, and methods disclosed herein may be used to monitor temperature in any suitable application in which the object to be measured has a dielectric property. Such other uses may include electrical monitoring applications (such as electrical insulator monitoring), general tissue temperature monitoring applications (e.g., cooking applications, checking temperature of non-cancerous cells), or other fields in which temperature monitoring may be utilized. In one embodiment, such other uses may include tracking heating of objects (e.g., components) within enclosures such as aircraft engines, computer, homes, among others. In other embodiments other forms of components, such as electrical components or structural components or other components, may be monitored. Thus the object to be monitored is not limited to tissue or cancer cells, and may include any object having a dielectric property. The object may comprise a general area to be measured having a dielectric property.

Exemplary Results

Figure 6:
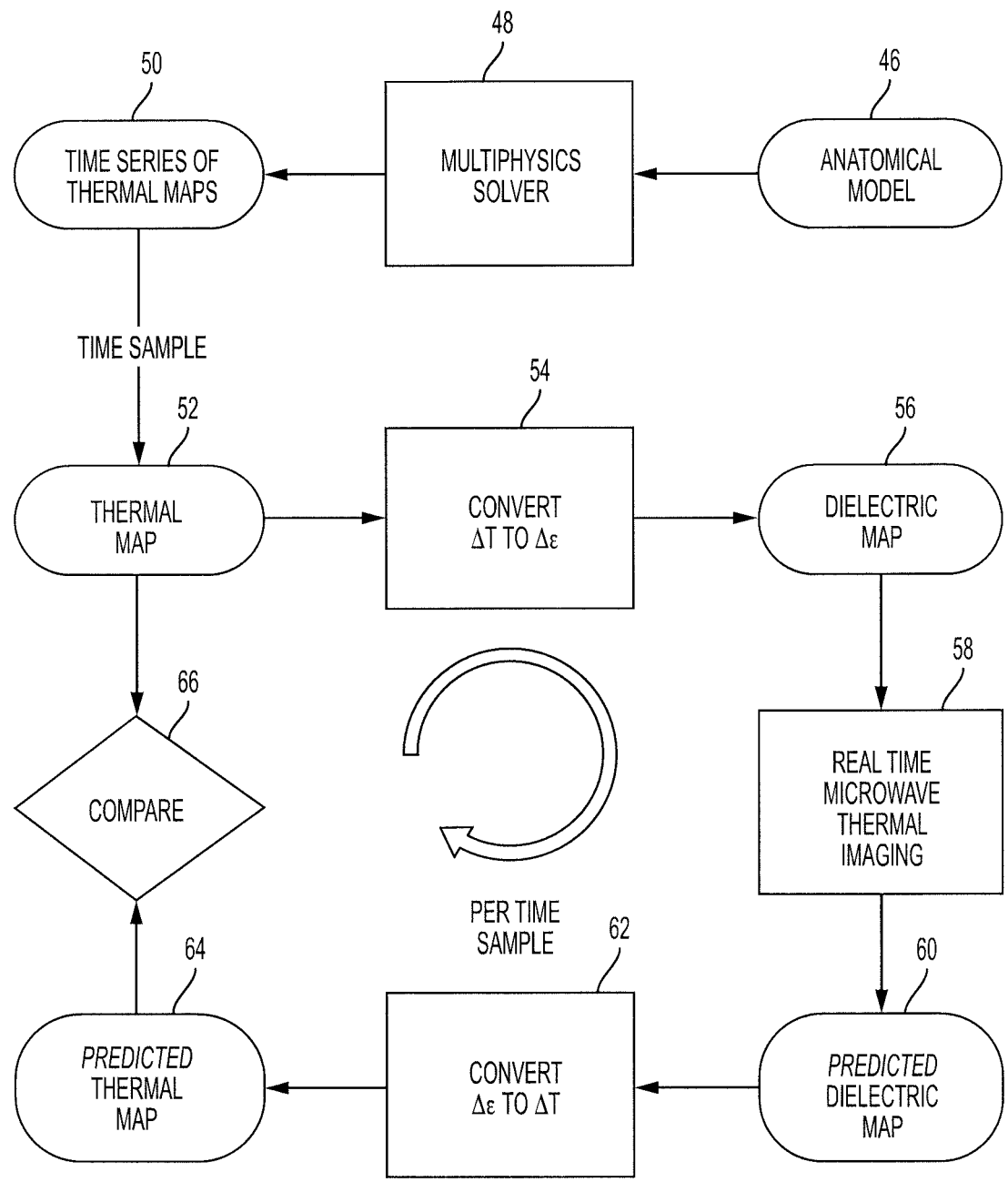
FIG. 6 illustrates a flow-chart of an experimental method according to an embodiment of the present disclosure.

An experiment was performed to demonstrate the benefit of utilizing the methods disclosed herein, and particularly the DBIM methods. The apparatuses, systems, and methods disclosed herein may be utilized with or in substitution of, or to vary, any other apparatus, system, or method disclosed herein. As an experiment, and with reference to FIG. 6, a time series of temperature maps was generated using an anatomically accurate multiphysics model of the thermal treatment of a brain lesion using a microwave probe. The use of the anatomical model is represented as step 46 in FIG. 6. The use of a multiphysics solver is represented as step 48 in FIG. 6. The time series of temperature maps are represented as step 50 in FIG. 6. This time series of temperature distributions was then used to create a corresponding series of dielectric maps of the treatment region and its surroundings. The time sample of temperature maps is represented as step 52 in FIG. 6. The correspondence between temperature and dielectric is represented as step 54 in FIG. 6. The formation of the dielectric maps is represented as step 56 in FIG. 6. Next, these dielectric maps were used as unknown objects to test the real time microwave imaging described herein. The real time microwave thermal imaging is represented as step 58 in FIG. 6. The predicted dielectric maps are represented as step 60 in FIG. 6. The recovered maps of dielectric were mapped back to predicted maps of change in temperature over time during the course of the thermal therapy. The mapping of dielectric to change in temperature is represented as step 62 in FIG. 6. The resulting predicted thermal map represented as step 64 in FIG. 6. The temperature maps predicted using real time microwave thermal imaging were then compared to the original maps. The comparison of the original maps to the predicted maps is represented as step 66 in FIG. 6. The procedure for each step is described further below.

Figure 7:
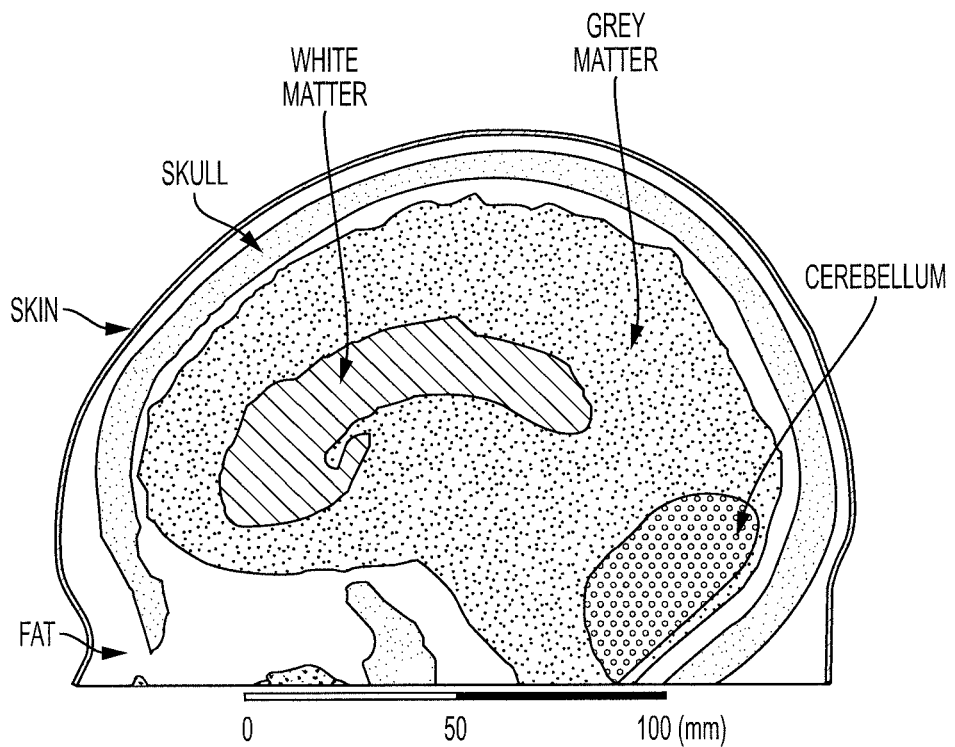
FIG. 7 illustrates a 2D slice of an anatomical model used in a multiphysics solver according to an embodiment of the present disclosure.
Figure 8A:
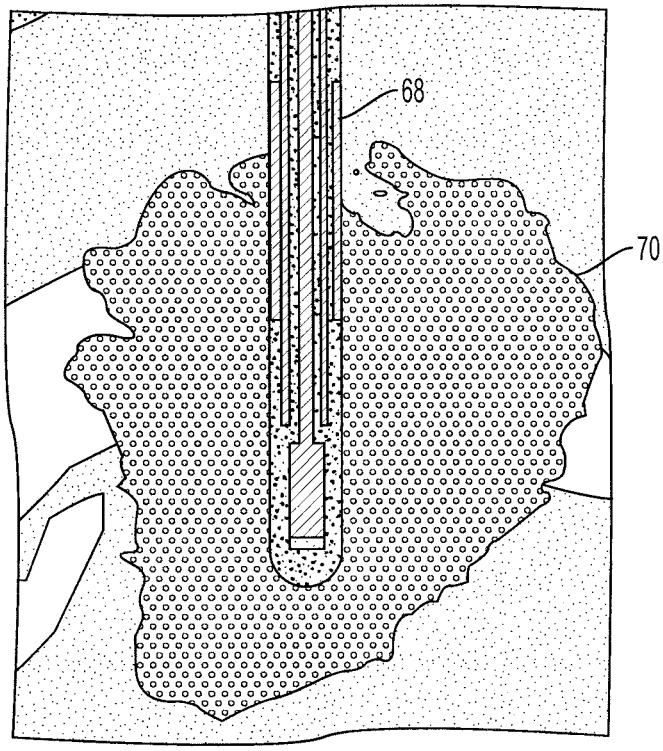
FIG. 8A illustrates a model of a probe in a tumor according to an embodiment of the present disclosure.

For the purposes of generating a realistic time series of heat maps for the case of thermal therapy in the brain, modeling of the heating of a brain tumor from a microwave probe in clinical use was performed, operating at 40 Watts of continuous power at a frequency of 1.9 GHz. To construct the background dielectric model of the head (as shown in FIG. 7), the VHP-Female 2.2 tissue-segmented FEM model sourced from the high-resolution cryosection image dataset from the Visible Human Project and validated by a board of medical experts, was used. The full geometry of the microwave probe 68, along with a tumor 70 model imported from the BRATS 2015 tumor database, were then added to the model, as shown in FIG. 8A. Then, published dielectric properties, shown in Table I below, were assigned to their respective tissue types. A voxelized version of this model was also used in the initialization of the forward scattering model.

TABLE I

DIELECTRIC PROPERTIES OF TISSUES IN ANATOMICAL PHANTOM

| Material | Electrical Permittivity | Electrical Conductivity |
| --- | --- | --- |
| Grey Matter | 52.3 | 0.99 S/m |
| White Matter | 38.6 | 0.62 S/m |
| Cerebellum | 48.9 | 1.31 S/m |
| Skin | 40.9 | 0.90 S/m |
| Fat | 5.5 | 0.05 S/m |
| Skull | 12.4 | 0.16 S/m |
| Eye | 68.9 | 1.67 S/m |
| Trachea (Air) | 1 | 0 S/m |
| Tumor | 70 | 2.0 S/m |

Figure 8B:
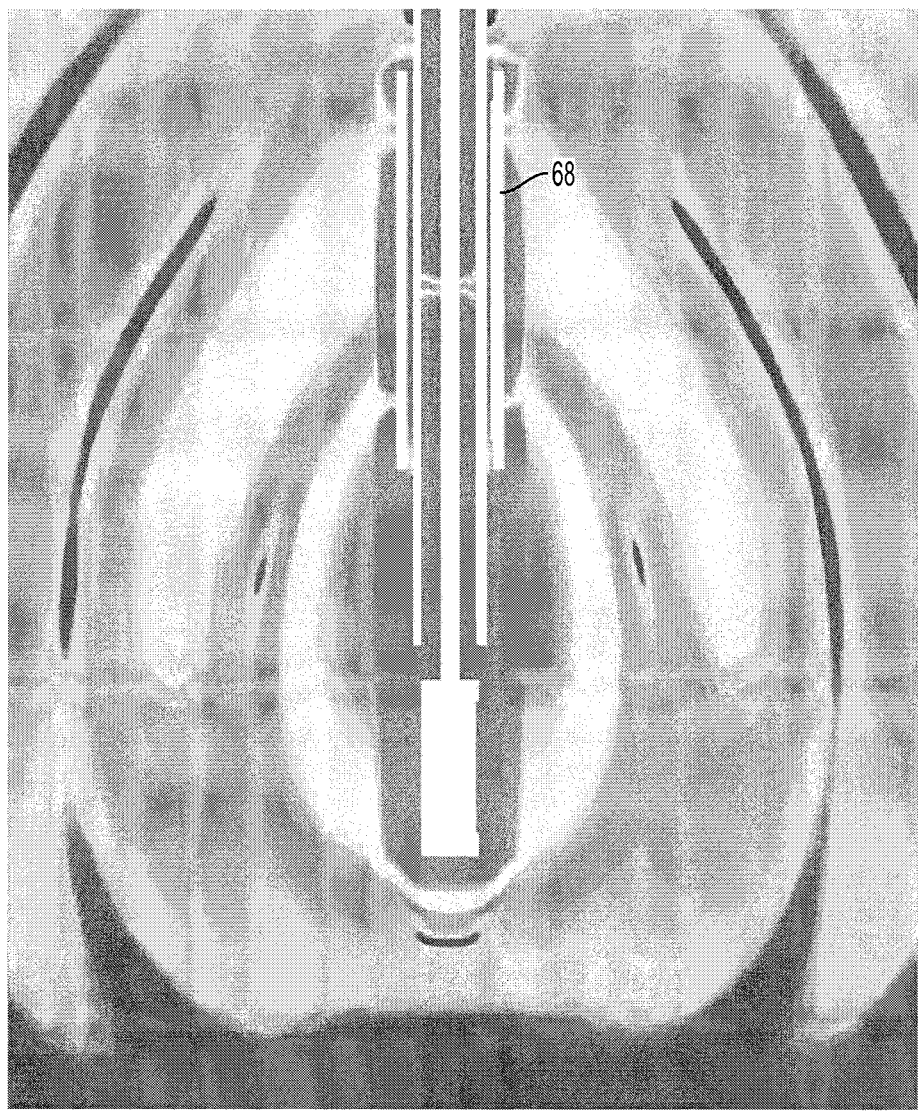
FIG. 8B illustrates a model of instantaneous electric field magnitude according to an embodiment of the present disclosure.

Using this anatomically realistic model, a time series of heat maps was generated in a two step process. First, the microwave power absorption in the heated region due to the microwave therapy probe was computed using a conformal FDTD solver (sample instantaneous electric fields around the probe 68 are shown in FIG. 8B). The modeled microwave power absorption was then used as a distributed heat source to solve Penne's Bioheat Equation in the time domain with CST Microwave Studio using the default material parameters for brain tissue and the initial and boundary temperatures set to 37° C.:

$$\rho c \frac{\partial T_t}{\partial t} = \nabla \cdot (k_t \nabla T_t) + \rho c \omega (T_a - T_t) + q_{met} + q_{ext} \quad (16)$$

where $\rho=1030$ kg/m$^3$ is the density of brain tissue, c=3675 J/K/kg is the specific heat of brain tissue, $k_t=1.13$ W/K/m is brain tissue thermal conductivity, $\omega=40$ kw/K/m$^3$ is the local blood perfusion rate, $T_t$ is the current tissue temperature, $T_a$ is the arterial blood temperature of 37° C., $q_{met}=7.1$ kW/m$^3$ is the local metabolic heat generation rate, and $q_t$ is the volumetric heat source due to the ablation probe.

The thermal distribution was recorded at several sample time steps and volumetric temperature maps at each time were exported to file at a 2 mm resolution. These temperature maps were then converted to dielectric maps as described below.

Figure 9:
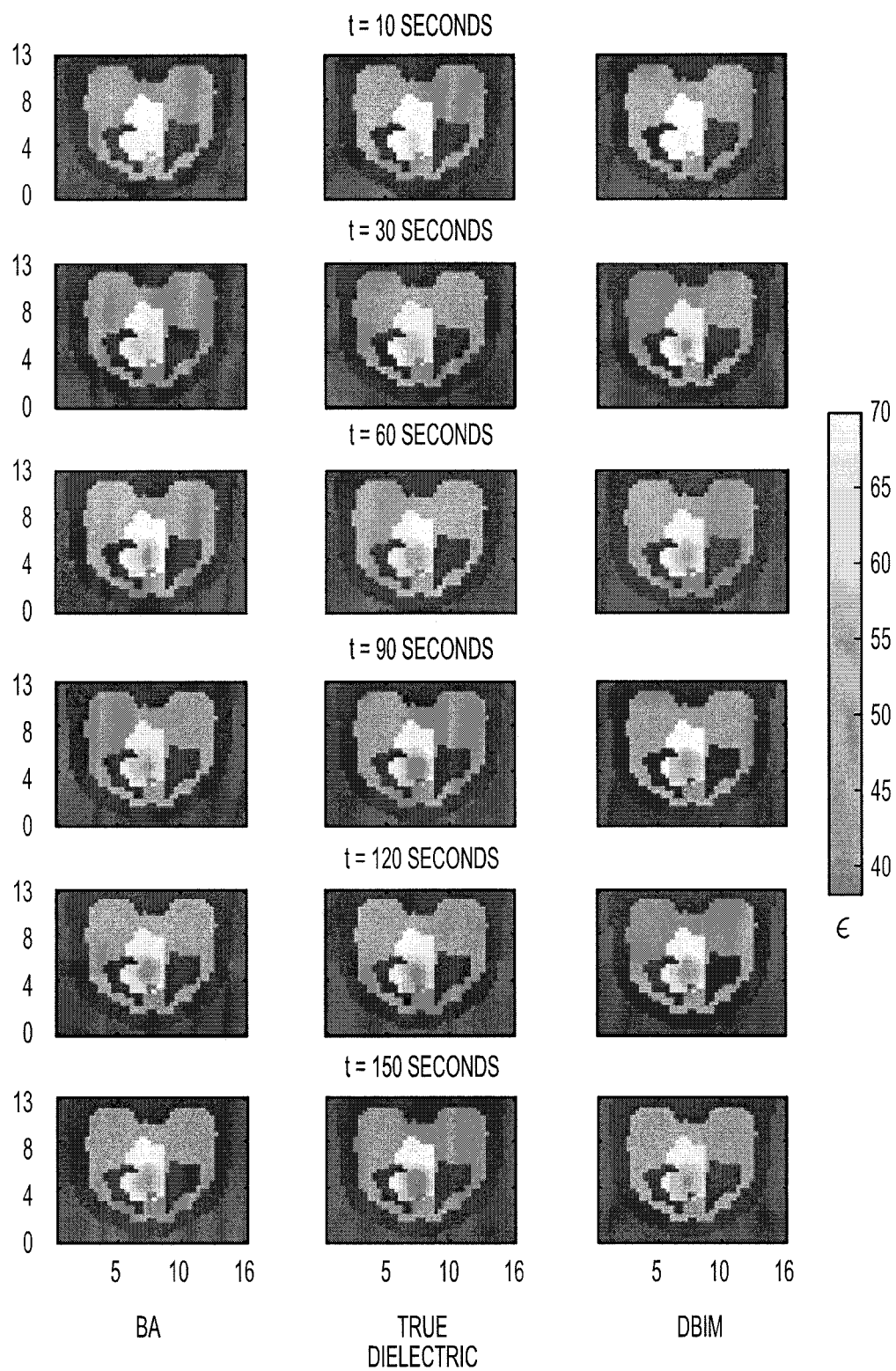
FIG. 9 illustrates a coronal slice of relative dielectric constant maps directly adjacent to a probe over time during thermal therapy, with spatial units in centimeters, according to an embodiment of the present disclosure.

Based on prior studies of the relationship between tissue temperature and dielectric, a decrease of 1% in complex dielectric (relative to the initial unheated dielectric of that tissue) per degree celsius increase in temperature, was applied. This relation is used to convert between temperature and dielectric in both the Multiphysics thermal model above and real-time microwave imaging. The resulting dielectric maps are shown in FIG. 9.

For the application of monitoring the thermal treatment of brain lesions, a microwave imaging cavity was utilized that is tailored to the geometry of the head. Other imaging cavity designs may be appropriate for the monitoring of therapies in other regions of the body, but the general principles remain the same. Here, the imaging cavity contained a total of 96 rectangular patch antennas whose geometries were optimized both for radiation efficiency and optimal modeling efficiency (i.e. alignment with CFDTD forward solver grid), which is also represented in FIG. 4. The antennas were arranged in 3 rows of 8 antennas each for 2 antennas on each of the four vertical sides of a 25×15×25 cm$^3$ cavity. The antenna measurements were taken at a single frequency of 880 MHz. In this validation, 36 antennas were used as transmitters and 36 were used as receivers, for a total of 1296 S-parameter measurements. The monitored region is a rectangular region of the size 4×5.3×4 cm$^3$ around the hottest spot of the heating probe. The location of the probe is assumed to be known and the probe is removed from the monitored region during the inversion process.

Here, the dielectric maps of the brain tissue during the thermal therapy are generated at 0, 5, 10, 20, 30, 60, 90, 120, and 150 seconds from the start of heating. The dielectric maps from these nine time frames are then imported to the CFDTD solver to simulate the S-parameters measurements between different transmitting and receiving antennas. As the inferred dielectric constant maps from the heat solver is on uniform 2 mm hexaheral mesh grid, while the CFDTD is on a nonuniform hexahedral mesh grid with cell length varying from 3.6 to 4.5 mm, sub-samples of the dielectric constant of the brain in each time slice inferred from the heat solver to the mesh grid of the CFDTD solver were performed using the nearest point method. It is assumed the location of heat probe is known and the probe area to be PEC throughout the simulation is enforced.

In the DBIM reconstruction, the forward problem is solved and time slices are imaged at 5, 10, 20, 30, 60, 90, 120, and 150 seconds. For each time slice, the reconstructed dielectric map and the total electric field in the monitored region from the previous time slice for reconstruction are used. The forward problem is solved more frequently at the early time, because the change of temperature is steeper. Lastly, since the temperature prediction is dependent on both the initial accuracy of the prior imaging study and the inferred dielectric properties of the tissue from that study, the entire procedure was repeated for the case where a 2% random error is assumed in the background dielectric map.

The results of the experiment for the proposed microwave thermal monitoring method is provided. The reconstructed dielectric and temperature maps using DBIM and BA are compared. The mean temperature within a defined treatment region is quantitatively evaluated, which represents how accurately we can monitor the thermal dose delivered in the region of interest (ROI). The mean percentage error of the reconstructed pixels within the monitored region is also evaluated, which demonstrates the accuracy of the reconstruction algorithm. Then, the evaluation of a reconstruction when there is a 2% error in the derived dielectric background from the imaging study at the beginning of the monitoring of process is presented.

First, a visual comparison of the reconstructed results using the BA real-time microwave imaging method and the DBIM method is provided. FIG. 9 shows a comparison between the actual and reconstructed relative dielectric constant maps over time for a coronal slice taken directly adjacent to the probe during thermal therapy. The center column shows actual values, the left column the reconstructed maps from the linear BA method, and the right column the maps from the nonlinear DBIM with asynchronous updates of the forward scattering model. Each dielectric map figure contains the reconstructed differential dielectric added to the current background dielectric (including the brain model). This creates the new dielectric background for the current time frame, which is then imported to the CFDTD forward solver to compute the new total field within the VIE to be used in the differential reconstruction in the next frame. As can be seen from FIG. 9, the dielectric map reconstructed using DBIM is visually closer to the true dielectric than the one using BA.

Figure 10:
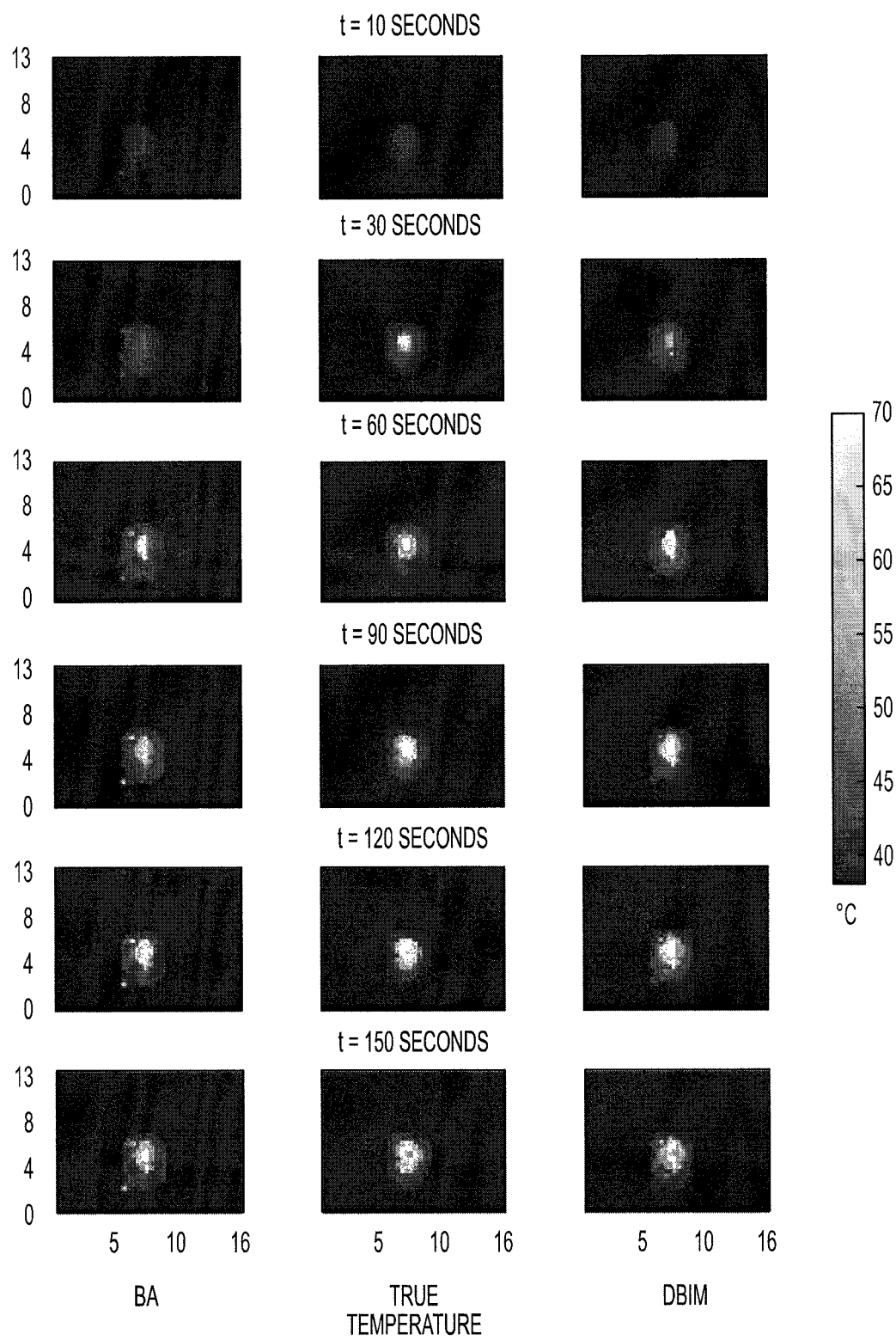
FIG. 10 illustrates a coronal slice of temperature maps directly adjacent to a probe over time during thermal therapy, with spatial units in centimeters, according to an embodiment of the present disclosure.

FIG. 10 illustrates a comparison between the corresponding actual and reconstructed temperature maps over time for the same coronal slice shown in FIG. 9. Again, the center column shows actual values, the left column the map from the prior method (BA), and the right column the temperature maps from the new method (DBIM). It is shown that the estimated temperature using DBIM is closer to the true temperature than the one derived from the BA method. After visually comparing the reconstructed results using the two methods, a quantitative comparison of the two methods may be provided. Here, the case may be added which has a 2% random error in the derived dielectric background from other imaging studies, where we are reconstructing using an erroneous dielectric background from the beginning of the monitoring.

Figure 11:
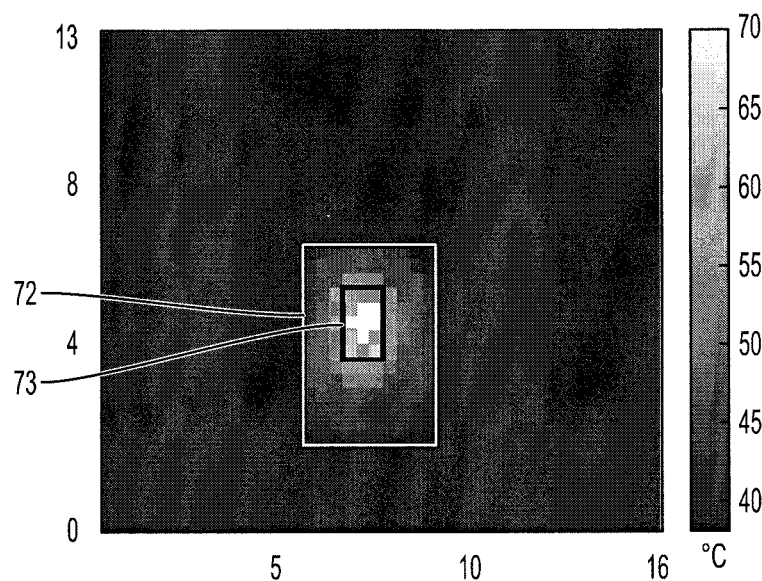
FIG. 11 illustrates a side view of a monitored region (within box 72) and region of interest (within box 73), with spatial units in centimeters, according to an embodiment of the present disclosure.

The mean temperature within a rectangular region of the size 1:2×1:8×1:2 cm$^3$ around the hottest spot of the thermal probe is then compared. A side view of this rectangular ROI is shown as the region within the box labeled 73 in FIG. 11. This ROI may be considered to be the treatment region, where the temperature of each pixel within this region is not more than 10 degrees lower than the hottest pixel throughout the treatment process. In addition, this ROI is defined within the resolution limit of the current monitoring system. With 880 MHz incident signal and a background dielectric value varying from 70 to 40 during the heating, the wavelength of electromagnetic wave is between 4.1 to 5.4 cm. The DBIM could reach a reasonably expected super-resolution of $0.25\lambda$ which is between 1.03 to 1.35 cm in this case. Thus an ROI is chosen that is within this monitoring resolution limit.

Figure 12:
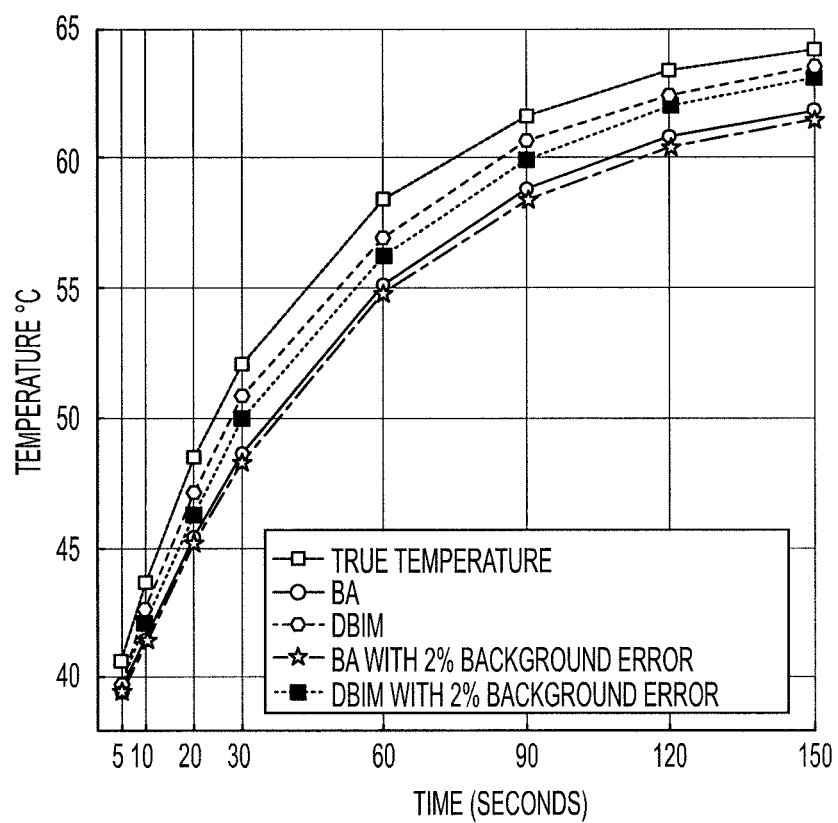
FIG. 12 illustrates a chart of the comparison of the mean temperature in region of interest over time, according to an embodiment of the present disclosure.

As shown in FIG. 12, both DBIM and BA tend to underestimate the temperature within the ROI which is expected from microwave inverse scattering using L2 noun in the cost function, which has an effect of low-pass filtering and spreading the energy of the object dielectric contrast. The reconstructed average temperature within the ROI using DBIM is closer to the true average temperature than the one obtained using BA, which means that the DBIM provides a better estimation of the thermal dose delivered to the ROI. The maximum estimation error of the mean temperature within the ROI through the monitoring process for BA, DBIM, BA with 2% background errors and DBIM with 2% background errors is 3.4, 1.5, 3.7, and 2.2 degrees, respectively. The average estimation error of the mean temperature within the ROI through the monitoring process for BA, DBIM, BA with 2% background errors and DBIM with 2% background errors is 2.5, 1.0, 2.9, and 1.7 degrees, respectively.

Figure 13:
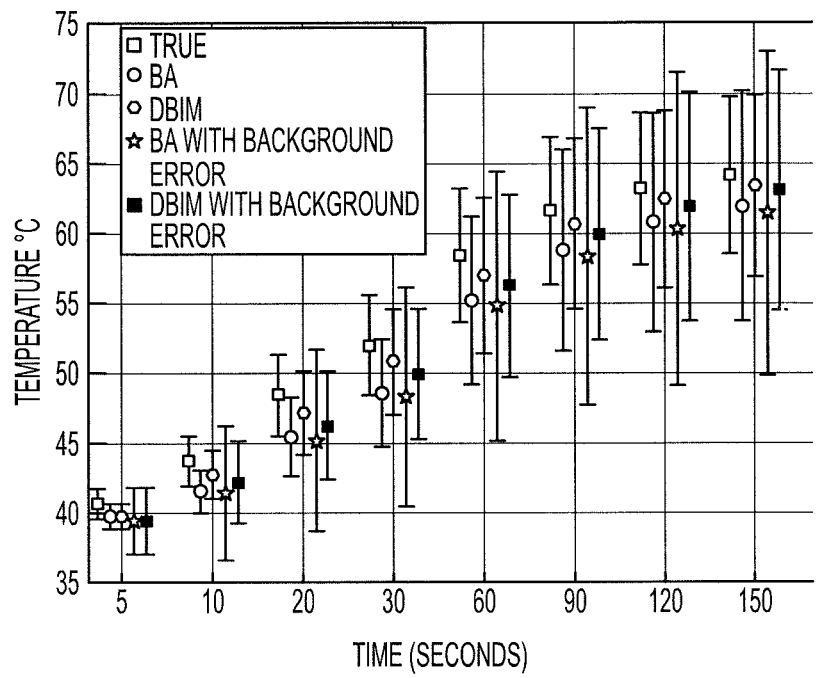
FIG. 13 illustrates a chart of the comparison of standard deviation of the temperature within the region of interest for all cases.

In addition to comparing the average temperature within the ROI, the standard deviation (STD) of the temperature within the ROI is evaluated for each case and compared with the true value. The standard deviation here is not an indication of uncertainty, but rather a measure of the spatial distribution of the temperature. As the region is heated, both the spatial gradient and variability of the temperature within the ROI increase, and as shown in FIG. 13, the DBIM method is more accurately capturing the distribution of the temperature within the ROI than the BA in both the noise-free and 2% noise case, respectively.

Figure 14:
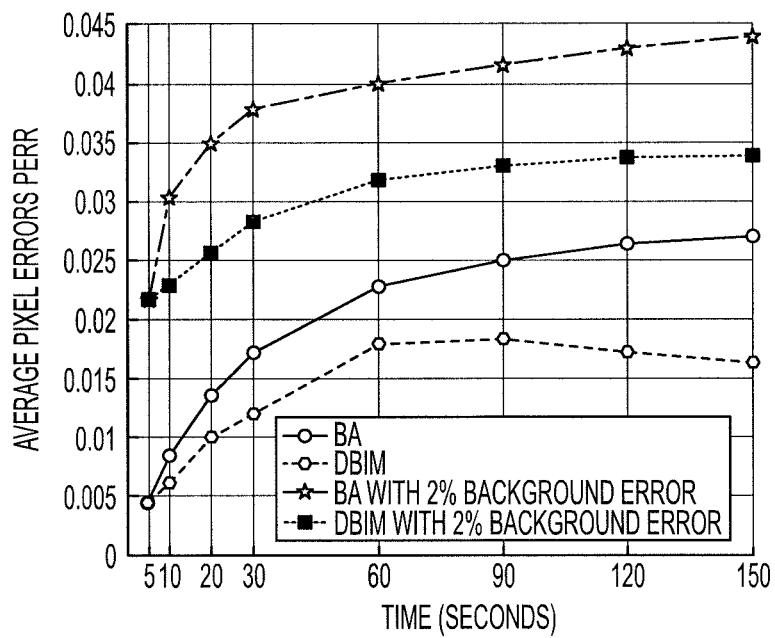
FIG. 14 illustrates a chart of the comparison of relative pixel percentage error of the monitored region.

The relative pixel error of the whole monitored region (as shown in the box 72 of FIG. 11 having dimensions of 4×5.3×4 cm$^3$) may be evaluated using each reconstruction method. As the expected resolution using 880 MHz signal is around 1.35 cm, while the pixel size of reconstructed image is around 0.42 cm, the small pixels from the image may be integrated to create large pixels closer to the size of resolution. The average relative error $P_{err}$ of the large pixel is defined in (17) below, $$P_{err} = \frac{1}{N}\sum_{i=1}^{N}\left|\frac{\int(\epsilon_{inv}(r) - \epsilon_{true}(r))dV^i}{\int \epsilon_{true}(r)dV^i}\right| \quad (17)$$

where $\in_{inv}$ and $\in_{true}$ is the reconstructed and true dielectric value of the pixel, respectively. $V^i$ is the area of the $i^{th}$ large pixel. Here, 3×3×3 small pixels may be integrated to obtain a large pixel. N is the number of large pixels within the monitored region. As shown in FIG. 14, the maximum relative pixel error of the 8 time frames using BA, DBIM, BA with 2% background error and DBIM with 2% background error are 2.7%, 1.8%, 4.4%, and 3.4%, respectively. These relative pixel errors are directly related to how accurate the temperature change is estimated. It is shown that DBIM outperforms BA with regard to the pixel reconstruction accuracy within the whole monitored region. The reasons may be two-fold, 1) during the inversion, the DBIM provides a better approximation of the total field within the VIE by solving the forward problem in each iteration, 2) compared to BA, DBIM can utilize evanescent waves and multiple scattering effects which provide increased resolution. The effect of the 2% background error from prior imaging studies is clearly shown from the start of the "BA with 2% background error" and "DBIM with 2% background error" error lines. This can be interpreted as an initial offset error, which may be correctable with in-situ calibration.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of systems, apparatuses, and methods as disclosed herein, which is defined solely by the claims. Accordingly, the systems, apparatuses, and methods are not limited to that precisely as shown and described.

Certain embodiments of systems, apparatuses, and methods are described herein, including the best mode known to the inventors for carrying out the same. Of course, variations on these described embodiments will become apparent to those of ordinary skill in the art upon reading the foregoing description. The inventors expect skilled artisans to employ such variations as appropriate, and the inventors intend for the systems, apparatuses, and methods to be practiced otherwise than specifically described herein. Accordingly, the systems, apparatuses, and methods include all modifications and equivalents of the subject matter recited in the claims appended hereto as permitted by applicable law. Moreover, any combination of the above-described embodiments in all possible variations thereof is encompassed by the systems, apparatuses, and methods unless otherwise indicated herein or otherwise clearly contradicted by context.

Groupings of alternative embodiments, elements, or steps of the systems, apparatuses, and methods are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses an approximation that may vary, yet is capable of performing the desired operation or process discussed herein.

The terms "a," "an," "the" and similar referents used in the context of describing the systems, apparatuses, and methods (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the systems, apparatuses, and methods and does not pose a limitation on the scope of the systems, apparatuses, and methods otherwise claimed. No language in the present specification should be construed as indicating any non-claimed element essential to the practice of the systems, apparatuses, and methods.

All patents, patent publications, and other publications referenced and identified in the present specification are individually and expressly incorporated herein by reference in their entirety for the purpose of describing and disclosing, for example, the compositions and methodologies described in such publications that might be used in connection with the systems, apparatuses, and methods. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A method for determining a change of temperature of an object, comprising:
    determining dielectric properties of the object before the heating of the object;
    forming a dielectric map of the object based on the dielectric properties of the object before the heating of the object;
    heating the object in a monitored region;
    measuring scattered S-parameters of scattered microwave electric fields from the object;
    iteratively updating a dielectric background and electric field of the monitored region based on the measured scattered S-parameters;
    determining a change of a dielectric property of the object based on the updated dielectric background and the updated electric field; and
    determining a change of temperature of the object based on the change of the dielectric property of the object.

2. The method of claim 1, wherein a vector network analyzer measures the scattered S-parameters.

3. The method of claim 1, wherein the object comprises tissue.

4. The method of claim 3, wherein the step of heating the object comprises interstitial thermal therapy.

5. The method of claim 1, wherein the updated dielectric background and the updated electric field are produced based on a distorted Born iterative method.

6. The method of claim 1, wherein the change of the dielectric property of the object is determined based on an electric field volume integral equation.

7. The method of claim 1, wherein the iterative update of the dielectric background and the electric field occurs asynchronously with the determination of the change of the dielectric property of the object.

8. The method of claim 1, wherein a graphic processing unit performs the iterative update of the dielectric background and the electric field in parallel with the determination of the change of the dielectric property of the object.

9. A method for determining a change of temperature of an object, comprising:
heating the object;
measuring scattered S-parameters of scattered microwave electric fields from the object;
utilizing a distorted Born iterative method to determine a change of a dielectric property of the object based on the measured scattered S-parameters, the distorted Born iterative method includes determining the change of the dielectric property of the object every i frame and updating a forward model every j frame; and
determining a change of temperature of the object based on the change of the dielectric property of the object.

10. The method of claim 9, wherein each i frame and each j frame occur asynchronously.

11. The method of claim 9, wherein forward model parameters are determined every j frame that are used in all subsequent i frames until the next j frame.

12. The method of claim 9, wherein a total electric field within an electric field volume integral equation and a differential imaging background are updated every j frame.

13. The method of claim 9, wherein the determination of the change of the dielectric property of the object every i frame, and the updating of the forward model every j frame, occurs in parallel.

14. A system comprising:
one or more antennas configured to receive scattered microwave electric fields from an object in a monitored region;
a controller configured to:
measure scattered S-parameters of the scattered microwave electric fields;
iteratively update a dielectric background and electric field of the monitored region based on the measured scattered S-parameters;
determine a change of a dielectric property of the object based on the updated dielectric background and the updated electric field; and
determine a change of temperature of the object based on the change of the dielectric property of the object; and
a graphical processing unit configured to perform the iterative update of the dielectric background and the electric field in parallel with the determine the change of the dielectric property of the object.

15. The system of claim 14, wherein the controller includes a vector network analyzer.

16. The system of claim 14, wherein the controller is configured to update the dielectric background and update the electric field based on a distorted Born iterative method.

17. The method of claim 14, wherein the controller is configured to perform the iterative update of the dielectric background and the electric field asynchronously with the determination of the change of the dielectric property of the object.

18. A method for determining a change of temperature of an object, comprising:
heating the object in a monitored region;
measuring scattered S-parameters of scattered microwave electric fields from the object;
iteratively updating a dielectric background and electric field of the monitored region based on the measured scattered S-parameters;
determining a change of a dielectric property of the object based on the updated dielectric background and the updated electric field; and
determining a change of temperature of the object based on the change of the dielectric property of the object,
wherein the iteratively updating of the dielectric background and the electric field is performed by a graphic processing unit in parallel with the determining the change of the dielectric property of the object.

19. The method of claim 18, wherein a vector network analyzer measures the scattered S-parameters.

20. The method of claim 18, wherein the object comprises tissue.

21. The method of claim 20, wherein the step of heating the object comprises interstitial thermal therapy.

22. The method of claim 18, further comprising determining dielectric properties of the object before the heating.

23. The method of claim 22, further comprising forming a dielectric map of the object based on the dielectric properties of the object before the heating.

24. The method of claim 18, wherein the updated dielectric background and the updated electric field are produced based on a distorted Born iterative method.

25. The method of claim 18, wherein the change of the dielectric property of the object is determined based on an electric field volume integral equation.

26. The method of claim 18, wherein the iterative update of the dielectric background and the electric field occurs asynchronously with the determination of the change of the dielectric property of the object.

* * * * *